United States Patent [19]
Hill et al.

[11] 3,988,457
[45] Oct. 26, 1976

[54] NOVEL COMPOUNDS AND COMPOSITIONS FOR TREATING PARKINSON'S DISEASE

[75] Inventors: Harlan F. Hill, Narberth; John J. Lafferty, Levittown, both of Pa.

[73] Assignee: SmithKline Corporation, Philadelphia, Pa.

[22] Filed: July 17, 1975

[21] Appl. No.: 596,872

Related U.S. Application Data

[62] Division of Ser. No. 440,431, Feb. 7, 1974, Pat. No. 3,919,230.

[52] U.S. Cl. .............................................. 424/250
[51] Int. Cl.² ..................................... A61K 31/495
[58] Field of Search ................................... 424/250

[56] References Cited

UNITED STATES PATENTS 3,299,067    1/1967    Regnier et al. .............. 260/256.4 N

*Primary Examiner*—Frederick E. Waddell
*Attorney, Agent, or Firm*—Joseph A. Marlino; Richard D. Foggio; William H. Edgerton

[57] ABSTRACT

β-Naphthylmethyl piperazinyl derivates having anti-Parkinsonism activity prepared by condensation of β-chloromethylnaphthalene with the appropriate substituted piperazine.

9 Claims, No Drawings

NOVEL COMPOUNDS AND COMPOSITIONS FOR TREATING PARKINSON'S DISEASE

This is a division of application Ser. No. 440,441 filed Feb. 7, 1974, which has issued into U.S. Pat. No. 3,919,230.

This invention relates to novel β-naphthylmethyl piperazinyl derivatives having valuable pharmacodynamic activity. More specifically, the compounds of this invention possess anti-Parkinsonism activity.

Parkinson's disease is a neurological disorder characterized by hypokinesia, akinesia, tremor and rigidity of the limbs. Parkinsonism is believed to be brought about by imbalance in the biochemical systems in the brain between the dopaminergic and cholinergic neural pathways. In patients suffering from Parkinsonism, a depletion of dopamine in the brain is observed which is the result of progressive degeneration of nigro-striatal dopaminergic neurons.

Prior to the present invention, there has been a great need for compounds and compositions which produce anti-Parkinsonism activity without having limiting side effects. It is well known that L-dopa, a potential source of brain dopamine, has clinical utility in treating Parkinsonism. The L-dopa is a precursor of dopamine and is decarboxylated in the brain to form dopamine, thereby raising the levels of dopamine in patients who are deficient in it. However, L-dopa does not qualify as an ideal compound in the treatment of Parkinsonism due in part to its limiting side effects, such as, for example, nausea, emesis and anorexia.

It is therefore the object of the present invention to provide dopaminergic-like compounds for the treatment of Parkinson's disease which do not possess the limiting side effects of L-dopa.

The compounds of this invention have been demonstrated as having anti-Parkinsonism activity without the corresponding side effects by employing a modified standard animal pharmacological test procedure reported by Ungerstedt et al., in *Brain Research* 24, 1970, 485–493. This test discloses a drug induced rotation of rats having extensive unilateral lesions of the substantia nigra. Briefly, the test comprises the quantitative recording of rotational behavior in rats after 6-hydroxydopamine lesions of the nigrostriatal dopamine system. A unilateral brain lesion in the left substantia nigra causes the dopamine receptor in the left caudate to become hypersensitive subsequent to the resulting degeneration of the nigral cell bodies. These lesions destroy the source of the neurotransmitter dopamine in the caudate but leave the caudate cell bodies and their dopamine receptors intact. Activation of these receptors by drugs which produce contralateral rotation, with respect to the lesioned side of the brain, is used as a measure of central dopaminergic activity of the drug.

Compounds which are known to be clinically effective in controlling Parkinsonism, such as, for example, L-dopa and apomorphine, are also effective in the rat turning model. These compounds directly activate the dopamine receptors and cause contralateral rotation of the lesioned rat.

Rotational activity is defined as the ability of a compound to produce 500 contralateral rotations during a two-hour period after administration, usually intraperitoneally. The dose corresponding to 500 contralateral rotations per two hours is obtained and assigned as the $RD_{500}$.

A preferred compound of this invention is 1-(β-naphthylmethyl)-4-(2-pyridyl) piperazine which produced and $RD_{500}$ of 8 mg./kg. as compared to 22.6 mg./kg. for L-dopa when tested in the above modified Ungerstedt test.

The compounds of this invention are represented by the following general structural formula:

Formula 1

in which
R represents phenyl, C pyridyl or C pyrimidinyl;
$R_1$ represents hydrogen, lower alkyl of 1–5 carbon atoms, straight or branched chain hydroxy, lower alkoxy of 1–5 carbon atoms, or halogen.

The pharmacodynamically active compounds of this invention have the basic structure of Formula 1. However, it is apparent to one skilled in the art that well known nuclear substituents may be incorporated on the phenyl, pyridyl or pyrimidinyl rings. Such substituents may be, for example, lower alkyl lower alkoxy, hydroxy or halogen. These substituted compounds are used as are the parent compounds.

Advantageous compounds of this invention are represented by the above structural formula when R represents C-pyridyl or C-pyrimidinyl and $R_1$ represents hydrogen.

The compounds of Formula 1 are prepared according to the following synthetic procedure:

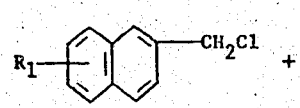

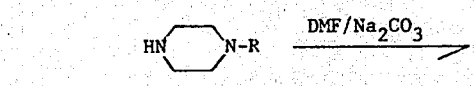

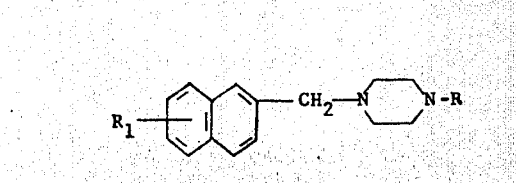

in which R and $R_1$ are as defined above.

The method is carried out using readily available starting materials and gives excellent yields of the end product. Where certain compounds desired for use as starting materials are not available, they can be prepared by methods described in the literature and well known to the art for preparing analogous compounds as described in the examples. Thus as shown above, a substituted chloromethylnaphthalene is reacted with the appropriate piperazinyl derivative in the presence of an organic solvent, such as, for example, dimethylformamide and an acid binding agent such as sodium or potassium carbonate, and heated to yield the desired compound. Alternatively the unsubstituted piperazine can be reacted with β-chloromethylnaphthalene to form β-(naphthylmethyl)piperazine which in turn can be reacted with the appropriately reactive R moiety.

The invention also includes nontoxic pharmaceutically acceptable addition salts of the above-defined bases formed with organic and inorganic acids. Such salts are easily prepared by methods known in the art. The base is reacted with either the stoichiometric amount of organic or inorganic acid in aqueous miscible solvent, such as acetone or ethanol, with isolation of the salt by concentration and cooling or an excess of the acid in aqueous immiscible solvent, such as ethyl ether or chloroform, with the desired salt separating directly. Exemplary of such organic salts are those with maleic, fumaric, benzoic, ascorbic, pamoic, succinic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic and theophylline acetic acids as well as with the 8-halotheophyllines, for example, 8-chlorotheophylline and 8-bromotheophylline. Exemplary of such inorganic salts are those with hydrochloric, hydrobromic, sulfuric, phosphoric and nitric acids. These salts may also be prepared by the classical method of double decomposition of appropriate salts which is well known to the art.

The novel compounds of this invention may be administered orally or parenterally in conventional dosage unit forms such as tablets, capsules, injectables or the like by incorporating the appropriate dose of a compound of Formula 1 with carriers according to the accepted pharmaceutical practices. The substituted β-naphthylmethyl piperazinyl derivatives will be present in an amount to produce anti-Parkinsonism activity. Preferably the dosage unit forms will contain the compounds of Formula 1 in an amount of from about 10 mg. to about 100 mg., advantageously from about 25 mg. to about 50 mg. Most advantageously equal daily doses are administered one to four times daily to provide a daily dosage regimen of from about 10 mg. to about 400 mg.

The pharmaceutical carrier employed may be, for example, either a solid or liquid. Exemplary of solid carriers are lactose, terra alba, talc, sucrose, gelatin, agar, pectin, acacia, magnesium stearate, stearic acid, and the like. Exemplary of liquid carriers are syrup, peanut oil, olive oil, water and the like. Similarly, the carrier as diluent can include any time delay material well known to the art such as glyceryl monostearate or glyceryl distearate alone or with a wax.

A wide variety of pharmaceutical forms can be employed. Thus if a solid carrier is used the preparation can be tableted, placed in a hard gelatin capsule in powder or pellet form or in the form of a troche or lozenge. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampule, or an aqueous liquid suspension.

The following examples illustrate the preparation of specific compounds having anti-Parkinsonism activity. However, this should not be construed as a limitation of the invention since other variations will be obvious to those skilled in the art.

EXAMPLE 1

To a mixture containing 5.0 g. of β-chloromethylnaphthalene, 3.0 g. of sodium carbonate and 30 ml. of dimethylformamide is added 4.6 g. of pyrimidinylpiperazine. The mixture is stirred and heated on a steam bath for approximately two hours. The mixture is then cooled, filtered and the filtrate is concentrated to a small volume in vacuo. The residue is washed with water and crystallized from ethanol to yield 1-(β-napthylmethyl)-4-(2-pyrimidinyl)-piperazine having a melting point of 109°–110° C.

An ethereal solution of the free base is treated with hydrogen chloride to yield the hydrochloride salt.

EXAMPLE 2

A mixture containing 7.0 g. of β-chloromethylnaphthalene, 6.56 g. of 2-pyridylpiperazine and 4.4 g. of sodium carbonate in 40 ml. of dimethylformamide is stirred on a steambath for 90 minutes. The reaction mixture is filtered and the filtrate stirred with ice water. The precipitate was filtered and recrystallized from isobutyl alcohol to yield 1-(β-napthylmethyl)-4-(2-pyridyl)piperazine having a melting point of 124°–126° C.

An acetone solution of the free base is reacted with succinic acid to yield the succinate salt.

EXAMPLE 3

A mixture of 10.0 g. of β-chloromethylnapthalene, 6.0 g. of sodium carbonate and 9.0 g. of phenylpiperazine in 60 ml. of dimethylformamide is stirred under nitrogen on a steambath for five hours. The reaction mixture is then cooled and filtered. The filtrate is concentrated and stirred with ice water. The formed precipitate is filtered off, dissolved in isobutyl alcohol and treated with ethereal hydrogen chloride to yield the hydrochloride salt of 1-(β-napthylmethyl)-4-(phenyl)-piperazine having a melting point of 226°–228° C.

EXAMPLE 4

Employing the procedure outlined above and using 10.9 g. of 1-(4-methoxyphenyl)piperazine as a starting material in place of phenylpiperazine yielded 1-(β-naphthylmethyl)-4-(4-methoxyphenyl)piperazine having a melting point of 117°–118° C.

EXAMPLE 5

Similarly using the above procedures, 9.8 g. of 1-(3-chlorophenyl)piperazine used as a starting material yielded 1-(β-naphthylmethyl)-4-(m-chlorophenyl)piperazine having a melting point of 114°–115° C.

EXAMPLE 6

A solution of 2.0 g. of 1-(β-naphthylmethyl)-4-(4-methoxyphenyl)piperazine as prepared in Example 4 in 100 ml. of hot 48% hydrogen bromide is refluxed for 2 hours. The solution is then cooled and filtered. The collected precipitate is then recrystallized from isobutyl alcohol to yield the dihydrobromide salt of 1-(β-naphthylmethyl)-4-(4-hydroxyphenyl)piperazine having a melting point of 225°–227° C.

EXAMPLE 7

A solution of 20.0 g. of β-chloromethylnaphthalene, 17.9 g. of piperazine dihydrochloride and 22.0 g. of piperazine hexahydrate in 55 ml. of methanol is refluxed for two hours. The solution is then cooled and filtered and the filtrate concentrated. The resulting solid is taken up in water and treated with 10% sodium hydroxide. The basic solution is extracted with chloroform and the fractions are combined, washed with water and dried. The oily material is distilled to give β-(napthylmethyl)piperazine.

A mixture of 4.5 g. of β-(naphthylmethyl)piperazine, 2.6 g. of 2-chloro-3-hydroxypyridine and 2.8 g. of sodium carbonate in 50 ml. of dimethylformamide is stirred on a steambath for four hours. The mixture is cooled and filtered. The filtrate is stirred with ice water and the formed precipitate is filtered, dissolved in isobutyl alcohol and treated with ethereal hydrogen chloride to form the hydrochloride salt of 1-(β-naphthylmethyl)-4-(3-hydroxy-2-pyridyl)piperazine.

EXAMPLE 8

To a mixture of 4.50 g. of 1-(β-napthylmethyl)-piperazine(as prepared in Example 7), 2.5 g. of 2-chloro-5-hydroxypyrimidine in 30 ml. of dimethylformamide is added 2.0 g. of sodium bicarbonate and the mixture is refluxed for six hours. The mixture is cooled and filtered and the filtrate concentrated to a small volume in vacuo. The concentrate is diluted with 100 ml. of water and the insoluble material is washed with water and hexane to yield 1-(β-napthylmethyl)-4-(5-hydroxy-2-pyrimidinyl)piperazine.

EXAMPLE 9

To a suspension of 2.7 g. of lithium aluminum hydride in 75 ml. of dry ether is added dropwise a solution containing 5.5 g. of 6-methyl-2-naphthoic acid in 75 ml. of dry ether. The mixture is refluxed for three hours, cooled, and treated with 10% sodium hydroxide solution. The mixture is then filtered and dried to yield 6-methyl-2-naphthalenemethanol.

20.3 g. of 6-methyl-2-naphthalenemethanol is dissolved in 100 ml. of dry benzene and to this solution is added 30 ml. of thionyl chloride. The solution is stirred for about one hour and concentrated to yield 2-chloromethyl 6-methylnaphthalene.

A mixture of 11.0 g. of 2-chloromethyl-6-methylnaphthalene, 7.0 g. of sodium carbonate and 10.0 g. of 2-pyridylpiperazine in 75 ml. of dimethylformamide is stirred for six hours. The reaction mixture is cooled, filtered and the filtrate is concentrated. The precipitate is then washed with water and crystallized from ethanol to yield 1-(6-methyl-β-naphthylmethyl)-4-(2-pyridyl)-piperazine.

EXAMPLE 10

In like manner using the procedure of Example 9, 5-methoxy-2-naphthoic acid and 7-chloro-2-naphthoic acid were employed as starting materials in place of 6-methyl-2-naphthoic acid to yield respectively 1-(5-methoxy-β-naphthylmethyl)-4-(2-pyridyl)piperazine, (7-chloro-β-naphthylmethyl)-4-(2-pyridyl)piperazine.

EXAMPLE 11

A solution of 3.4 g. of 1-(5-methoxy-β-naphthylmethyl)-4-(2-pyridyl)piperazine in 100 ml. of 48% hydrogen bromide is refluxed for 3 hours. The mixture is cooled, concentrated and treated with sodium carbonate. The mixture is extracted with chloroform and the chloroform extractions are dried to yield 1-(5-hydroxy-β-naphtylmethyl)-4-(2-pyridyl)piperazine.

EXAMPLE 12

| Ingredients | Mg./Tablet |
|---|---|
| 1-(β-naphthylmethyl)-4-(2-pyridyl)piperazine | 25 mg. |
| Calcium sulfate dihydrate | 100 mg. |
| Sucrose | 25 mg. |
| Starch | 15 mg. |
| Talc | 5 mg. |
| Stearic acid | 3 mg. |

The sucrose, calcium sulfate and 1-(β-naphthylmethyl)-4-(2-pyridyl)piperazine are thoroughly mixed and granulated with hot 10% gelatin solution. The wetted mass is passed through a No. 16 U.S. standard mesh screen directly onto drying trays. The granules are dried at 120° F. and passed through a No. 20 U.S. standard mesh screen. These granules are then mixed with starch, talc and stearic acid, passed through a No. 60 U.S. standard mesh screen and compressed into tablets.

One tablet is administered four times a day.

EXAMPLE 13

The above ingredients are thoroughly mixed and filled into a No. 2 hard gelatin capsule.

One capsule is administered twice a day.

| Ingredients | Mg./Capsule |
|---|---|
| 1-(β-naphthylmethyl)-4-(2-pyrimidinyl)piperazine | 50 mg. |
| Lactose | 200 mg. |

What is claimed is:

1. A pharmaceutical composition in dosage unit form having anti-Parkinsonism activity comprising a pharmaceutical carrier and an effective amount of a compound of the formula:

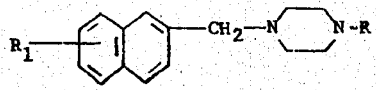

or a pharmaceutically acceptable acid addition salt thereof in which:

R is phenyl, pyridyl or pyrimidinyl; and
R₁ is hydrogen, lower alkyl, halogen, hydroxy or lower alkoxy having from 1 to 5 carbon atoms.

2. A pharmaceutical composition in accordance with claim 1 in which R₁ is hydrogen.
3. A pharmaceutical composition in accordance with claim 2 in which R is pyridyl.
4. A pharmaceutical composition in accordance with claim 3 in which R is 2-pyridyl.
5. A pharmaceutical composition in accordance with claim 4 in which said compound is in the form of a free base.
6. A method of producing anti-Parkinsonism activity which comprises administering internally to animals suffering from Parkinson's disease an amount sufficient to produce said activity a chemical compound having the formula:

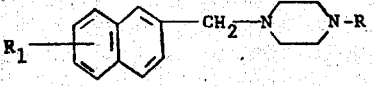

or a pharmaceutically acceptable acid addition salt thereof in which:
  R is phenyl, pyridyl or pyrimidinyl; and
  $R_1$ is hydrogen, lower alkyl, halogen, hydroxy or lower alkoxy having from 1 to 5 carbon atoms.
7. A method in accordance with claim 6 in which $R_1$ is hydrogen.

8. A method in accordance with claim 7 in which R is pyridyl.
9. A method in accordance with claim 8 in which R is 2-pyridyl.

* * * * *